(12) United States Patent
Holley et al.

(10) Patent No.: US 11,191,920 B2
(45) Date of Patent: Dec. 7, 2021

(54) BREATHABLE GAS VALVE DEVICE FOR RESPIRATORY TREATMENT APPARATUS

(71) Applicant: ResMed Pty Ltd, Bella Vista (AU)

(72) Inventors: Liam Holley, Marrickville (AU); Simon Robert Cork, Wollstonecraft (AU); Sebastien Deubel, Caringbah (AU)

(73) Assignee: ResMed Pty Ltd

(*) Notice: Subject to any disclaimer, the term of this patent is extended or adjusted under 35 U.S.C. 154(b) by 590 days.

(21) Appl. No.: 16/301,975

(22) PCT Filed: May 16, 2017

(86) PCT No.: PCT/AU2017/050445
§ 371 (c)(1),
(2) Date: Nov. 15, 2018

(87) PCT Pub. No.: WO2017/197446
PCT Pub. Date: Nov. 23, 2017

(65) Prior Publication Data
US 2019/0111232 A1 Apr. 18, 2019

Related U.S. Application Data

(60) Provisional application No. 62/337,405, filed on May 17, 2016.

(51) Int. Cl.
*A61M 16/20* (2006.01)
*A61M 16/08* (2006.01)
*A61M 16/00* (2006.01)

(52) U.S. Cl.
CPC ...... *A61M 16/206* (2014.02); *A61M 16/0858* (2014.02); *A61M 16/0069* (2014.02);
(Continued)

(58) Field of Classification Search
CPC .. A61M 16/206; A61M 16/207; A61M 16/00; A61M 2205/0222; A61M 2205/0238; A61M 2205/3334
See application file for complete search history.

(56) References Cited

U.S. PATENT DOCUMENTS

| 3,799,185 A | 3/1974 | Milnes et al. |
| 4,190,045 A | 2/1980 | Bartels |
| (Continued) | | |

OTHER PUBLICATIONS

International Search Report for International Application No. PCT/AU2017/050445, dated Aug. 22, 2017.
(Continued)

*Primary Examiner* — Kendra D Carter
*Assistant Examiner* — Thomas W Greig
(74) *Attorney, Agent, or Firm* — Botos Churchill IP Law LLP

(57) ABSTRACT

A respiratory valve, such as a positive end expiratory pressure valve, permits pressure control for respiratory apparatus such as a ventilator or positive airway pressure device. The valve may include a flexible gas passage cover. The cover may be configured with a first side surface to operatively block and open an aperture of the gas passage at a valve seat to respectively prevent and permit gas flow through the aperture defined by the valve seat. The cover may include a second side surface opposite the first surface. The second surface may include at least one drop section forming a reduction in thickness of the cover between the first surface and the second surface. The first surface may include a coating to reduce friction of a membrane material of the first surface. The rim of the valve seat may comprise a variation in height relative the flexible cover.

17 Claims, 14 Drawing Sheets

(52) U.S. Cl.
CPC ... *A61M 16/205* (2014.02); *A61M 2016/0027* (2013.01); *A61M 2016/0033* (2013.01); *A61M 2016/0042* (2013.01); *A61M 2205/0222* (2013.01); *A61M 2205/0238* (2013.01); *A61M 2205/3334* (2013.01); *A61M 2205/42* (2013.01)

(56) References Cited

U.S. PATENT DOCUMENTS

| | | | |
|---|---|---|---|
| D268,048 S | 2/1983 | Ueda | |
| 4,454,893 A * | 6/1984 | Orchard | A61M 16/20 128/205.24 |
| D290,640 S | 6/1987 | Andersson | |
| D316,292 S | 4/1991 | Baker | |
| 5,020,532 A | 6/1991 | Mahoney et al. | |
| 5,201,492 A | 4/1993 | Beauvir | |
| 5,535,987 A | 7/1996 | Wlodarczyk | |
| D382,943 S | 8/1997 | Doughty et al. | |
| 6,371,117 B1 | 4/2002 | Lindqvist et al. | |
| D470,226 S | 2/2003 | Herbert | |
| D585,968 S | 2/2009 | Elkins et al. | |
| D636,059 S | 4/2011 | Shorey et al. | |
| 8,251,960 B2 | 8/2012 | Mcconnell et al. | |
| D688,372 S | 8/2013 | Matheny | |
| D694,408 S | 11/2013 | Matheny | |
| D701,944 S | 4/2014 | Kahn | |
| D718,862 S | 12/2014 | Matheny | |
| D739,499 S | 9/2015 | Shorey et al. | |
| D765,854 S | 9/2016 | Blain et al. | |
| D783,167 S | 4/2017 | Falkenberg | |
| D785,766 S | 5/2017 | Sato | |
| D790,062 S | 6/2017 | Blain et al. | |
| D790,705 S | 6/2017 | Matheny et al. | |
| 2004/0069305 A1 * | 4/2004 | Niemela | A61M 16/205 128/205.24 |
| 2010/0199991 A1 * | 8/2010 | Koledin | A61M 16/208 128/205.12 |
| 2015/0038046 A1 | 2/2015 | Lindberg | |
| 2015/0136141 A1 | 5/2015 | Mittelstadt | |
| 2017/0284244 A1 | 10/2017 | Bock et al. | |
| 2017/0319977 A1 | 11/2017 | Barone | |

OTHER PUBLICATIONS

Prosthetic Valve. "Prosthetic Heart Valves", www.circ.ahajournals.org. Web, Mar. 5, 2018, Shown in p. 1 (2018).

\* cited by examiner

BREATHABLE GAS VALVE DEVICE FOR RESPIRATORY TREATMENT APPARATUS

CROSS-REFERENCES TO RELATED APPLICATIONS

The present application is a national phase entry under 35 U.S.C. § 371 of International Application No. PCT/AU2017/050445 filed May 16, 2017, published in English, which claims the benefit of and priority from U.S. Provisional No. 62/337,405, filed May 17, 2016 and entitled "Breathable Gas Valve Device for Respiratory Treatment Apparatus," all of which are incorporated herein by reference.

FIELD OF THE TECHNOLOGY

The present technology relates to valves for controlling gas flow in respiratory treatment apparatus. More specifically, it relates to valves to limit gas flow, such as for example an outlet for expiratory gas flow, for a flow generator in respiratory treatment apparatus such as positive airway pressure treatment devices, ventilator devices or other airflow devices for treating respiratory-related conditions.

BACKGROUND OF THE TECHNOLOGY

Respiratory treatment apparatus can function to supply a patient with a supply of clean breathable gas (usually air, with or without supplemental oxygen) at a therapeutic pressure or pressures, at appropriate times during the subject's breathing cycle. Pressure changes may be implemented in a synchronized fashion so as to permit greater pressures during inspiration and lower pressures during expiration. Therapeutic pressure is also known as the ventilation pressure.

Respiratory treatment apparatus, or systems, typically include a flow generator, an air filter, a patient interface, (e.g., mask), an air delivery conduit or patient circuit connecting the flow generator to the patient interface, various sensors and a microprocessor-based controller. Optionally, in lieu of a mask, a tracheotomy tube may also serve as a patient interface. The flow generator may include one or more blowers, e.g., a servo-controlled motor, volute and an impeller that forms the blower. The one or more blowers may be controlled to deliver or control desired inspiratory and/or expiratory pressures. The sensors measure, amongst other things, motor speed, mass flow rate and outlet pressure, such as with a pressure transducer or the like. The apparatus may optionally include a humidifier and/or heater elements in the path of the air delivery circuit. The controller may include data storage capacity with or without integrated data retrieval and display functions.

In some cases the flow generator may also include an expiratory valve capable of controlling end expiratory pressure. The valve when coupled to a patient circuit, such as a patient interface, can open to discharge expiratory air to atmosphere at desired pressures, which may be elevated above atmospheric pressure. Such a valve may be controlled by a positive end expiratory pressure blower. Such increased pressures can have a therapeutic effect, such as assisting with maintaining open patient respiratory airway(s).

These devices may be used for the treatment of many conditions, for example respiratory insufficiency or failure due to lung, neuromuscular or musculoskeletal disease and diseases of respiratory control. They may also be used for conditions related to sleep disordered breathing (SDB) (including mild obstructive sleep apnea (OSA)), allergy induced upper airway obstruction or early viral infection of the upper airway.

It may be desirable to develop further methods and devices for controlling the flow of breathable gas in a respiratory treatment apparatus during operations.

SUMMARY OF THE TECHNOLOGY

An aspect of some embodiments of the current technology is to provide a flow control device for a respiratory treatment apparatus.

Another aspect of some embodiments of the technology is to provide an outlet for a respiratory treatment apparatus.

Some versions of the present technology may include a valve device for a gas passage of a respiratory treatment apparatus that is configured to provide a flow of breathable gas to a patient. The valve device may include a valve seat defining an aperture of the gas passage for the flow of breathable gas. The valve device may include a flexible gas passage cover. The cover may include a first side surface to operatively block and open the aperture of the gas passage at the valve seat to respectively prevent and permit gas flow through the aperture of the gas passage. The flexible gas passage cover may include a second side surface opposite the first side surface. The cover may include at least one drop section including a reduction in a thickness between the first side surface and the second side surface.

In some versions, the cover may include a plurality of drop sections. Optionally, each drop section of the plurality of drop sections may comprise a sector. The cover may include a plurality of first sectors and a plurality of second sectors, the first sectors being raised in relation to the plurality of second sectors. The plurality of first sectors may be four sectors. The plurality of second sectors may be four sectors. The drop sections of the plurality of drop sections may have equal dimensions. Optionally, a drop section may include a nested drop section. The gas passage and the valve seat may be within a removable module. The gas passage may be configured as an expiratory gas passage. The gas passage may be configured as an inspiratory gas passage. The valve device may also include a pressure chamber adjacent to the second side surface of the cover to apply a confined operational gas pressure to the second side surface of the cover.

In some versions, the flexible gas passage cover may be configured as a circular disk. The circular disk may include a peripheral ring. The valve seat may include a circular rim. The first side surface of the cover may include a coating to reduce a coefficient of friction of a membrane material of the first side surface of cover.

Some versions of the present technology may include a valve device for a gas passage of a respiratory treatment apparatus that is configured to provide a flow of breathable gas to a patient. The valve device may include a gas passage. The valve device may include a valve seat that defines an aperture of the gas passage. The valve device may include a flexible gas passage cover configured with a first side surface for operatively blocking and opening the aperture of the gas passage at the valve seat to respectively prevent and permit gas flow through the aperture of the gas passage. The flexible gas passage cover may include a second side surface opposite the first side surface.

In some versions, the valve seat may include a cover contact rim comprising, or formed to have, a variation in height in relation to an imaginary plane formed by the first side surface of the flexible gas passage cover. The variation in height may form a wavy surface on the cover contact rim. The gas passage may be configured as an expiratory gas passage. The gas passage may be configured as an inspiratory gas passage. The valve device may also include a pressure chamber adjacent to the second side surface of the cover to apply a confined operational gas pressure to the second side surface of the cover. Optionally, the first side surface of the cover may include a coating to reduce a coefficient of friction of a membrane material of the first side surface of the cover.

Some versions of the present technology may include a valve device for a gas passage of a respiratory treatment apparatus that is configured to provide a flow of breathable gas to a patient. The valve device may include a flexible gas passage cover. The cover may be configured with a first side surface for operatively blocking and opening an aperture of the gas passage at a valve seat to respectively prevent and permit gas flow through the aperture of the gas passage. The aperture may be defined by the valve seat. The flexible gas passage cover may include a second side surface. The second side surface may be opposite the first side surface. The first side surface of the cover may include a coating to reduce a coefficient of friction of a membrane material of the first side surface of the cover.

In some versions, the coating may include talcum powder. The coating may include a silicone dispersion. The valve device may also include the gas passage and the valve seat. The gas passage may be configured as an expiratory gas passage. The gas passage may be configured as an inspiratory gas passage. The valve device may also include a pressure chamber adjacent to the second side surface of the cover to apply a confined operational gas pressure to the second side surface of the cover. The flexible gas passage cover may be configured as a circular disk, and may be generally flat.

Some versions of the present technology may a positive airway pressure apparatus. The apparatus may include a flow generator adapted to provide a supply of pressurized breathable gas to a patient interface. The apparatus may include a controller to control the level of pressure generated by the flow generator. The positive airway pressure apparatus may further include any valve device previously described and/or described further herein in more detail.

Additional features of the present respiratory treatment apparatus technology will be apparent from a review of the following detailed discussion, drawings and claims.

BRIEF DESCRIPTION OF DRAWINGS

The present technology is illustrated by way of example, and not by way of limitation, in the figures of the accompanying drawings, in which like reference numerals refer to similar elements including:

FIG. 14 shows the removable gas valve device of FIG. 13 partially installed in the RPT; and.

DETAILED DESCRIPTION

Figure 1:
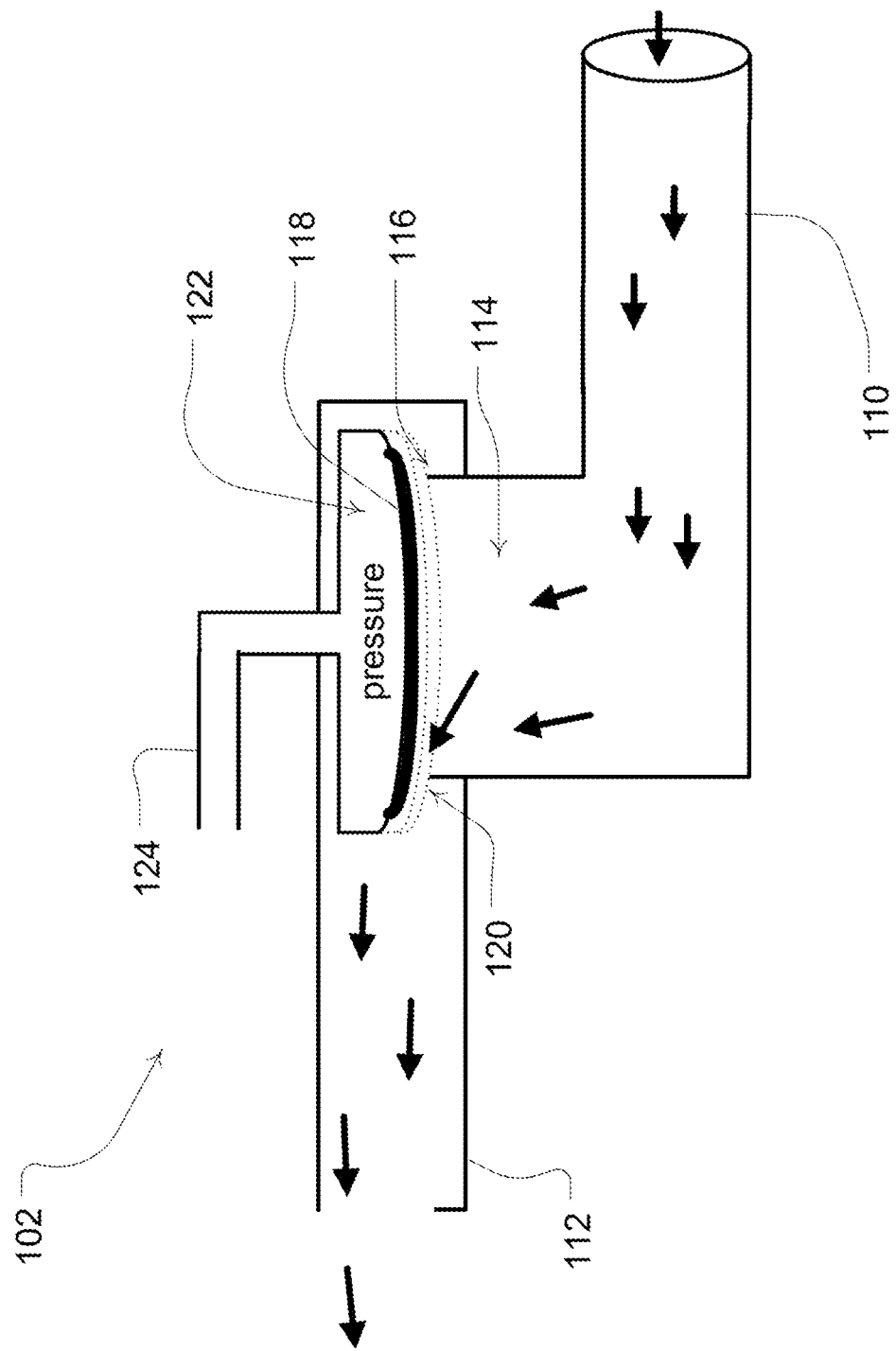
FIG. 1 is a schematic diagram illustrating components of an gas valve device for a flow generator in an embodiment of the present technology with a valve membrane for permitting passage of gas at a desired pressure.

Example embodiments of the current technology may be considered in relation to a breathable gas control valve device 102 for a flow generator or a respiratory treatment apparatus with one more of the components illustrated in the schematic diagram of FIG. 1. The valve device, such as when configured to operate as an expiratory valve 402 or 1302 as illustrated in FIGS. 4A and 13-15, may include an inlet 110 and an outlet 112, such as an outlet to atmosphere. The inlet 110 may be coupled to receive gas from an expiratory conduit of a patient circuit (e.g., connected to a patient mask). Between the inlet and outlet there is a gas passage 114 having a valve seat 116. The gas passage may be an expiratory passage in the case of implementation of an expiratory valve or and inspiratory passage in the case of implementation of an inspiratory valve. A flexible cover 118 or valve membrane, such as one formed of a flexible membrane, serves as a cover or cap to operatively narrow or widen (e.g., open and close) the aperture 120 to vary (e.g. permit or prevent) gas flow through aperture 120. The aperture 120 is defined by the valve seat 116 located at one side surface of the cover 118. The valve seat may serve as a rim about the periphery of the aperture 120. The rim has a surface for sealing contact with a surface of the cover.

As illustrated in FIG. 1, the flexible cover 118, such as at its opposite side surface, may also be pneumatically coupled to a pressure chamber 122. The chamber may have a pressure conduit 124 to supply a desired pressure contained within the pressure chamber 122. Optionally, the pressure set within the chamber 122 may be controlled by a blower, such as a positive end expiratory pressure blower coupled to the chamber by the pressure conduit 124. The pressure set within the pressure chamber affects operation of the cover membrane so as to permit the cover to open/close the aperture depending on patient generated pressures, such as expiratory air pressure exhaled by a user, provided into the valve at the inlet 110 and adjacent to the valve seat side of the cover. In this regard, greater relative pressure within the pressure chamber 122 impedes movement of the flexible cover 118 so that higher patient generated air pressures within the gas passage 114 of the inlet are required to move the cover from the valve seat and thereby open the aperture 120 of the gas passage to permit patient generated air to pass through the aperture to the outlet.

Figure 2:
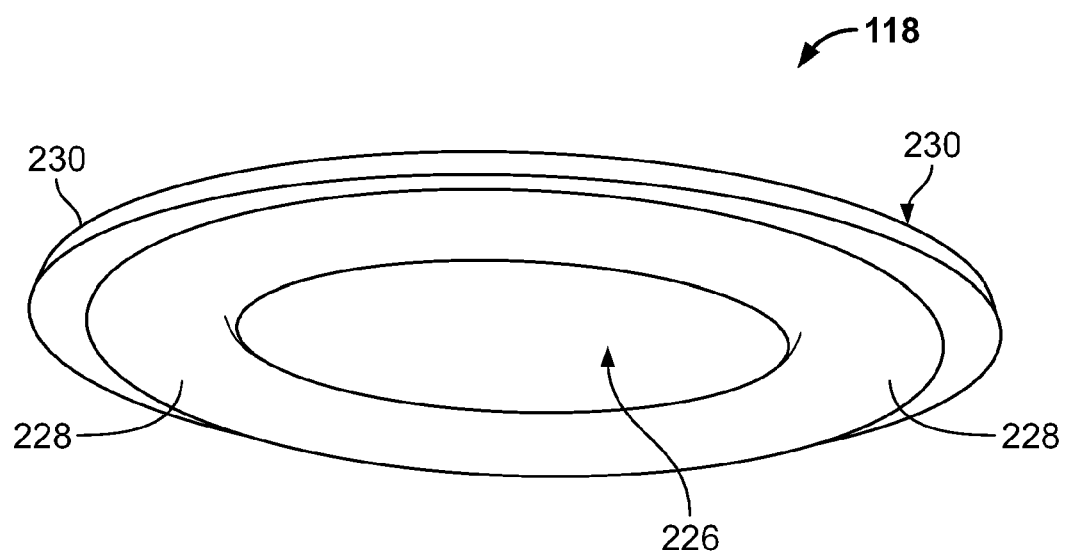
FIG. 2 is an isometric view of a valve membrane in some forms of the present technology.
Figure 3:
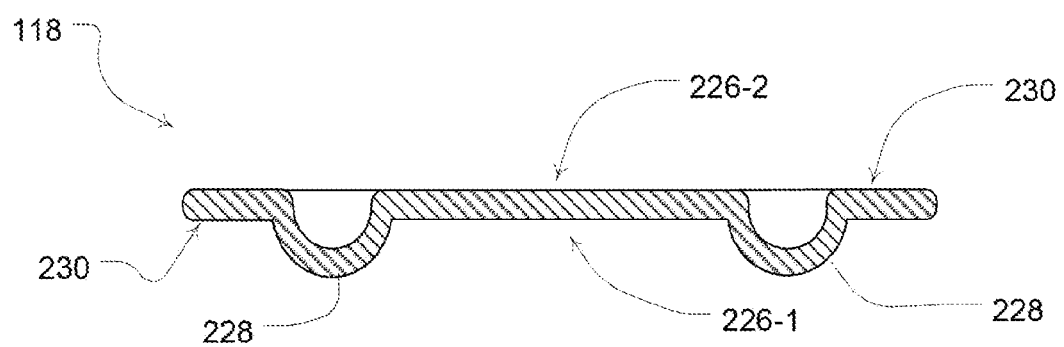
FIG. 3 is a side cross sectional view of the valve membrane of FIG. 2 taken along a diameter of the valve membrane.

An exemplary circular or disk-shaped membrane cover that may be implemented as the flexible cover 118 in some versions is illustrated in FIGS. 2 and 3. The cover may be formed as a membrane, of a flexible material such as an elastomeric material. The material may be for example, silicone, Ethylene Propylene Diene Monomer, Fluoroelastomers, Neoprene, Natural rubber or Fluorosilicone rubber. The thickness (cross sectional depth) of the material of the membrane may be in a range of about 0.1 mm to 3 mm, such as between 0.5 mm to 2 mm, although others may also be suitable. The cover may have a first surface 226-1 and a second surface 226-2, which may be substantially parallel to the first surface, and/or face the opposite direction to the first surface. The first surface may be of a suitable configuration (e.g. size and shape), so as to serve as a cap for closing the gas passage 114 by making a sealing contact with a periphery of the valve seat at its rim. Such a first surface may be considered a valve seat surface side. For example, the first surface 226-1 may be generally flat such that it may generally occupy an imaginary plane, such as when in a relaxed state. The second surface 226-2 may reside within or be proximate to the pressure chamber 122 when installed within a valve device. Thus, the second surface may be a pressure chamber surface side.

In some cases, the central cap area 226 may have a generally uniform material thickness, such as that illustrated in FIG. 3. Optionally, the cover may have a bellows region 228 or expansion region about the central cap area 226 such as one formed as a peripheral ring surrounding the central cap area 226 of the cover. The bellows region may be characterized by a thinner membrane thickness than the other areas of the membrane cover to provide a greater flexibility in this region. The bellows region may in some cases comprise a similar membrane thickness as the other areas of the membrane cover, while comprising a curvature configured to provide a greater flexibility in this region than other areas of the membrane cover. The cover membrane may also have a mounting edge 230. The mounting edge may extend about the periphery of the disk-shaped cover and may serve as a support for mounting of the cover on a complementary receiving structure within a valve device. The flexibility of the expansion region at the peripheral ring permits movement of the central cap area of the membrane relative to the mounting edge 230, such as in a direction parallel to a normal of the central cap area 226.

The cover membrane may be assembled to be in contact with the rim, which may be circular, of the aperture to be closed. However, it may be deformed (e.g., by deformation of the bellows region) so as to open the aperture due to greater pneumatic pressure in the inlet relative to the pneumatic pressure of the pressure chamber. The resilience of the cover membrane may be configured to bias the cover membrane towards the rim of the valve seat. Thus, the cover membrane may return to being in contact with the rim of the valve seat upon equalization of pressures between the pressure chamber and the inlet, or, in some cases even when pneumatic pressure is, to some degree, greater in the inlet relative the pneumatic pressure of the pressure chamber.

In some cases, valves employing membrane covers, such as those just described, can produce undesirable noise during use. This operation of an exemplary expiratory valve 402 having a cover membrane may be considered in reference to FIGS. 4 and 5. The expiratory valve 402 is similar to the valve described in reference to FIG. 1. However, the expiratory valve 402 is also shown with optional differential pressure sensing ports 461 and 463 for sensing of expiratory flow rate across flow limiting element 462. The valve also includes an expiratory pressure sensing port 465 for sensing expiratory pressure in the expiratory valve.

Figure 4C:
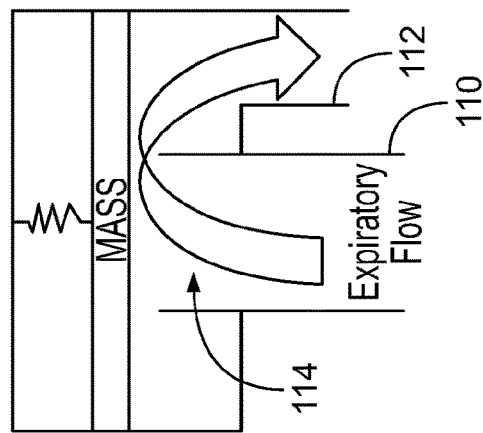
FIG. 4C illustrates modelling of the operation of the valve membrane of FIG. 4A as a mass and spring.
Figure 4B:
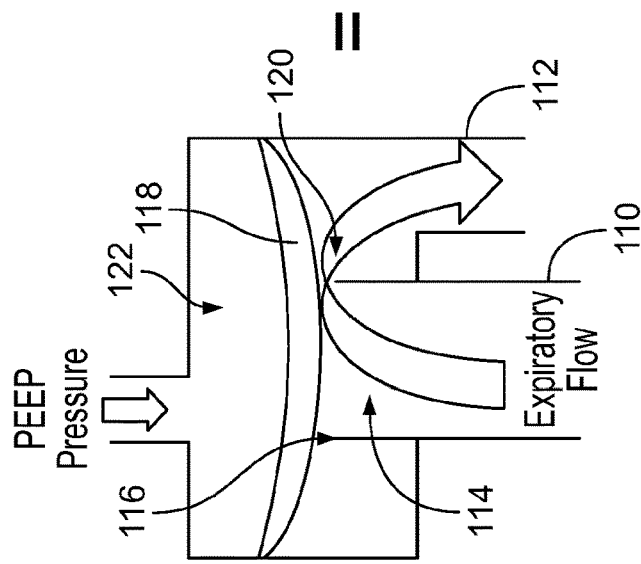
FIG. 4B illustrates operation of the valve membrane of FIG. 4A.
Figure 4A:
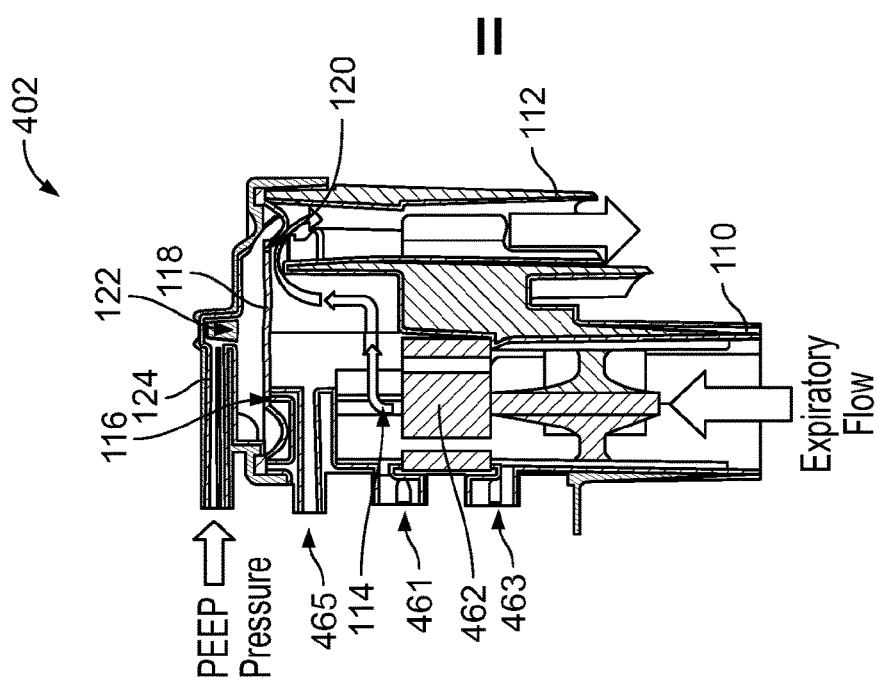
FIG. 4A shows a cross sectional view of an example gas valve device of FIG. 1 configured as an expiratory valve 402, such as with the valve membrane of FIG. 2.
Figure 5:
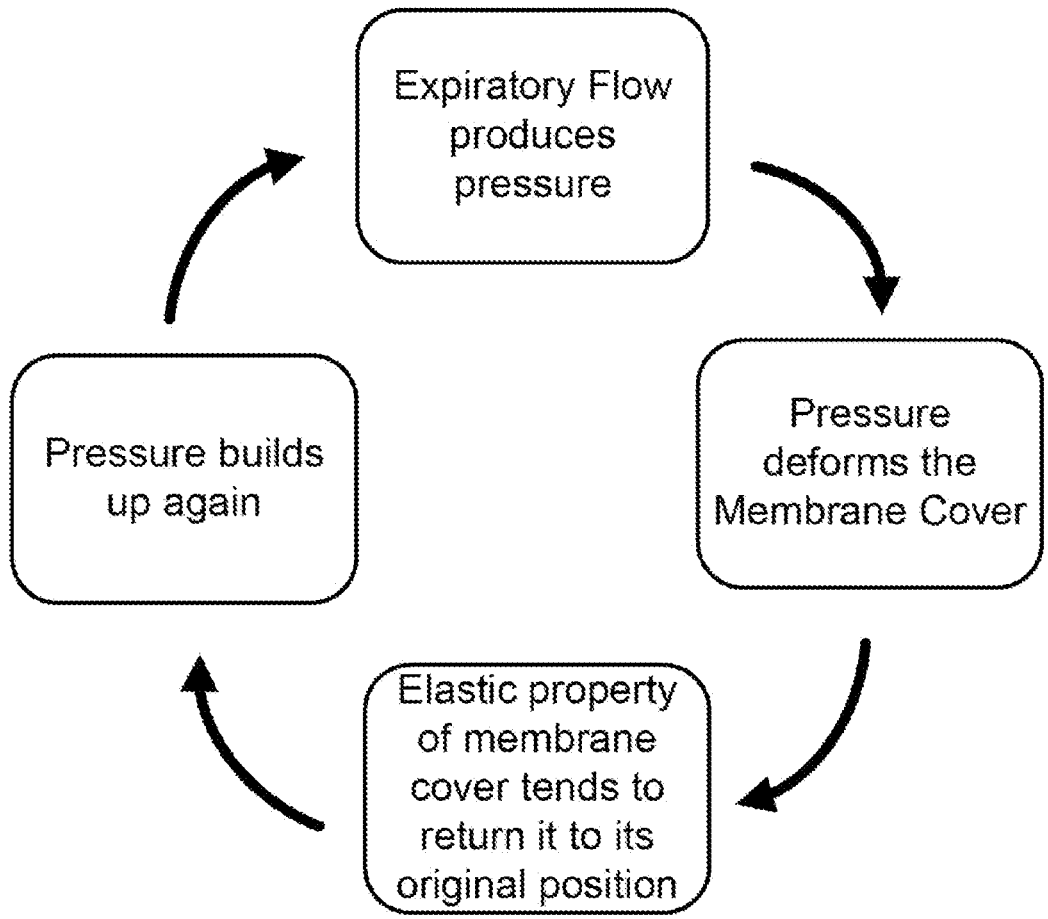
FIG. 5 is a chart illustrating an operational cycle of the expiratory valve of FIG. 4A.
Figure 6:
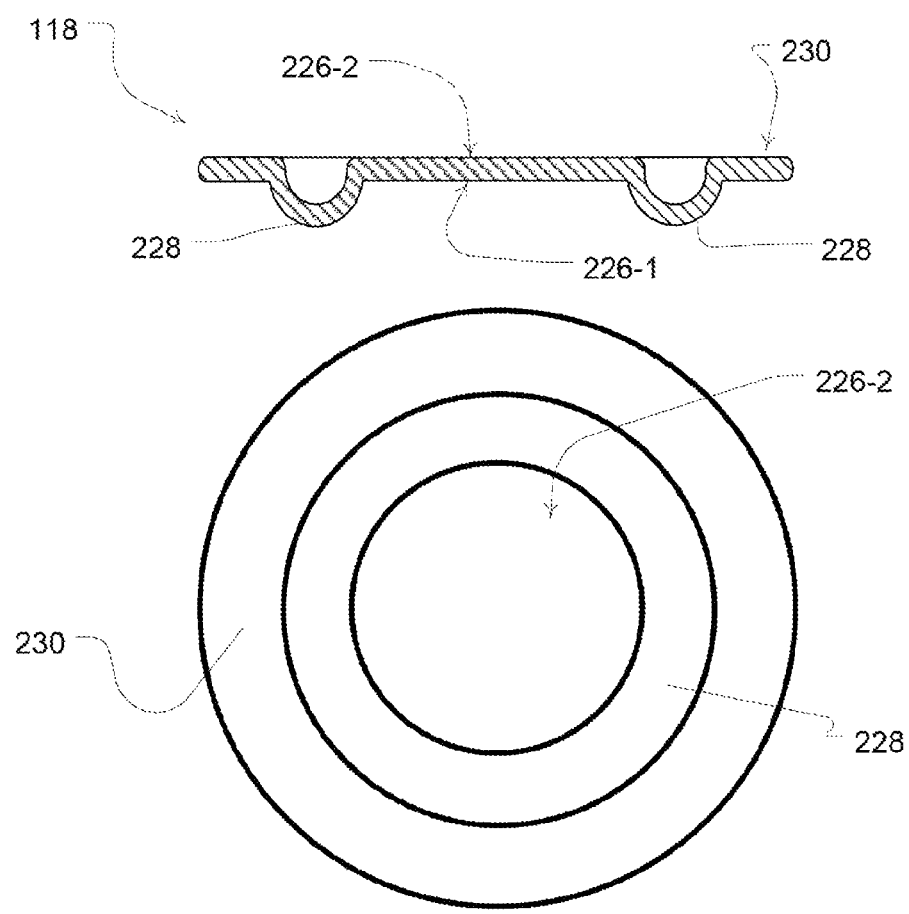
FIG. 6 is a further plan view illustration of the valve membrane of FIG. 4A, along with its cross section and a model of its operation as a mass, spring and damper.
Figure 6:
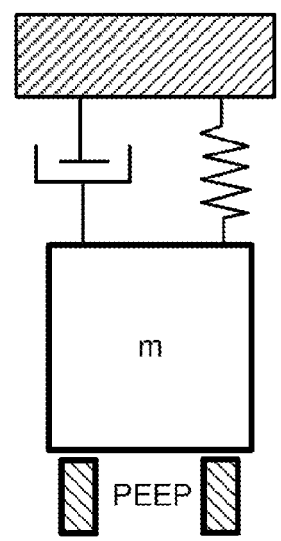

As illustrated in FIGS. 4A-4C, the flexible cover 118 and its associated pressure chamber 122 when serving as an expiratory valve may be modeled as uniform or constant mass and a spring, coupled to the pressure chamber 122. An operational cycle of that mass and spring may also be considered in reference to FIG. 5. The performance of such a membrane cover may also be modeled as a spring mass and damper as illustrated in FIG. 6 that reflects the combined effects of the elements of the system, including friction, membrane resilience, air pressure, deformation losses, etc.

For example, when configured as an expiratory valve 402, the membrane cover 118 can flutter and resonate in the valve so as to create a sharp tone, for example, at a particular frequency (e.g., 780 Hz) during patient expiration. In this regard, such an expiratory valve receives the expiratory flow from the patient (See, e.g., FIG. 4B) and the expiratory flow produces a pressure across the membrane cover which then deforms the membrane to open the covered aperture 120. Such an opening can then begin to decrease the pressure in the gas passage 114 permitting the membrane to move to close the aperture. In this regard, the elastic properties of the membrane return the membrane to its original position and the cycle can repeat, such as during a single expiration from a user. This cycle can accelerate as the membrane gets closer to the valve seat 116. The frequency of movement of the membrane can end up matching the natural resonance frequency of the membrane causing the membrane to resonate to create the sharp tone. This may be perceived by a user as undesirable device noise. Such noise may be particularly problematic for a medical device, which the patient may have to rely on to ameliorate or treat a medical condition, such as during sleep. Such devices may thus be in use for extended periods, prolonging the users' exposure to undesirable noise, and may also be deployed where there is only low levels of ambient noise, potentially worsening the perception of noise to the user. Accordingly, in some versions of the present technology, modifications are made to reduce or prevent resonance that might create a sharp tone.

For example, in some versions of the present technology, the cover membrane may include features to change stiffness/flexibility in relation to other areas of the cover membrane. For example, such features may be formed in portions of the central cap area of the cover membrane. Such features may form areas of the membrane having less mass and/or levels of stiffness compared to the mass and level of stiffness of other areas of the membrane.

Figure 7:
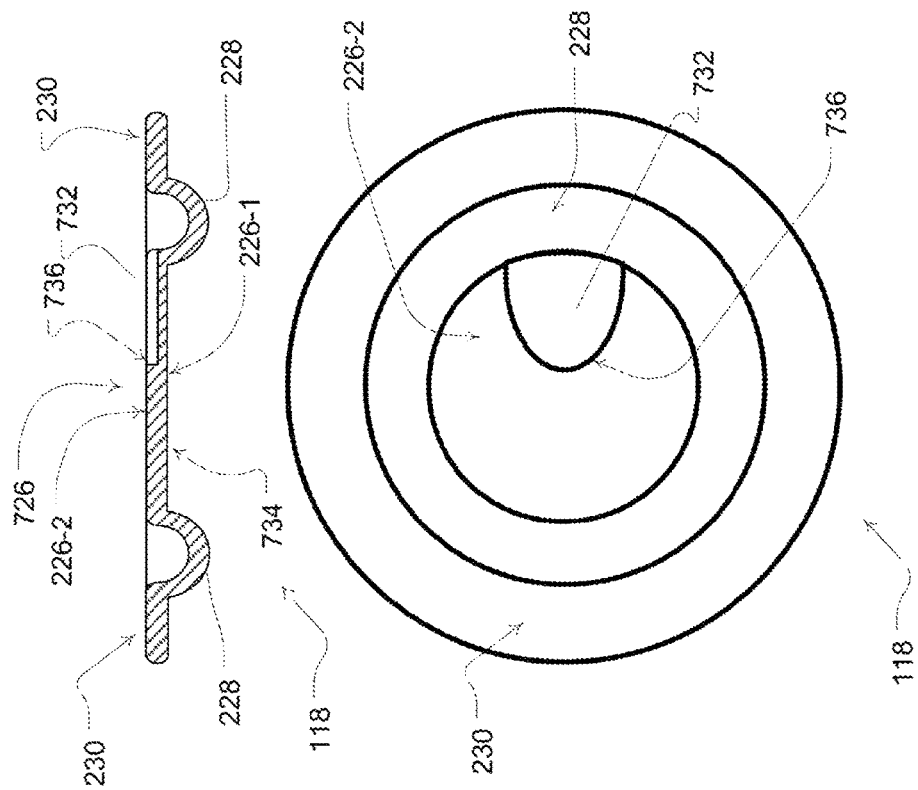
FIG. 7 is an illustration of a plan view and diameter cross sectional view of a modified valve cover membrane having a drop section to change an operational characteristic of the membrane.

In one version illustrated in FIG. 7, a portion of the surface of the membrane cover may include a drop section 732. The drop section may form an area (i.e. a portion) having a reduction in a thickness of the flexible gas passage cover between the first side surface and the second side surface of the membrane (in comparison to an adjacent portion, or a non-drop section). The drop section may be an area of the surface of the membrane cover of generally constant thickness and/or flexibility. In this regard, the drop section may be separated from another surface portion of the cover membrane by a substantially discrete, or step change, in thickness. The drop section may be in the central cap region 726. The drop section 732 may be formed on the top surface of the cover membrane that is opposite to the valve seat surface side 734 of the cover membrane. Thus, the valve seat surface side 734 of the cover membrane may remain generally flat or otherwise configured for making a sealing contact with the valve seat at its rim. Generally, the drop section may form a ridge 736 of deviation along a peripheral edge of the drop section. The rise of the ridge can be characterized by the difference in thickness between another portion of the membrane cover in the cap region and the thickness of the drop section.

Figure 8A:
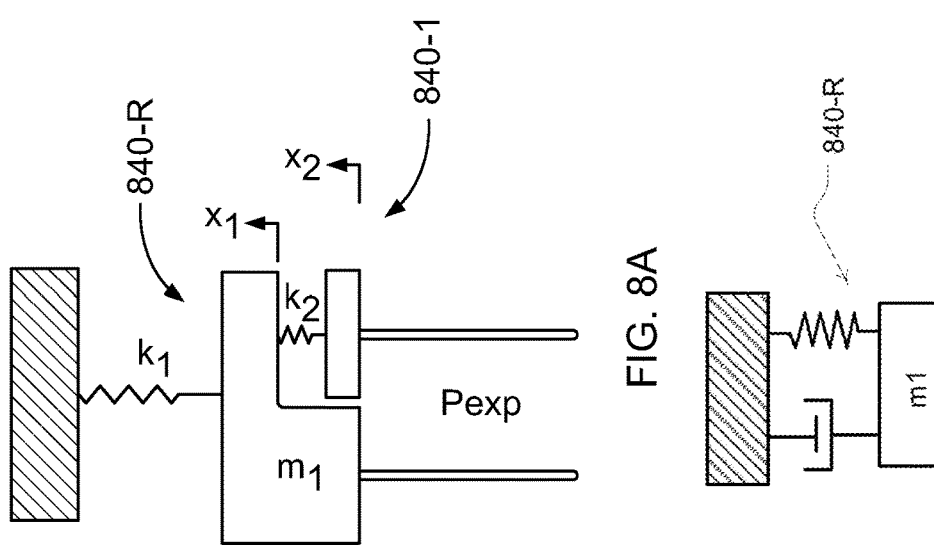
FIG. 8A is a further illustration of a simplified model of the operational configuration of the modified valve cover membrane of FIG. 7, modeled as masses and springs.
Figure 8B:
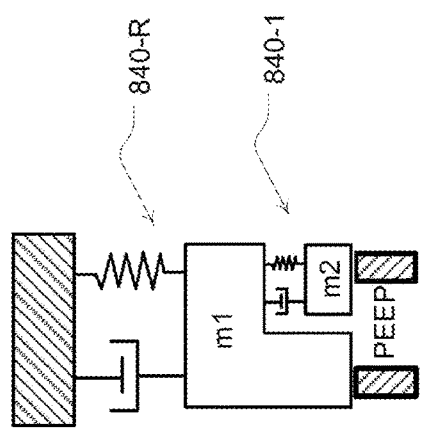
FIG. 8B illustrates a model of the operational configuration of the modified valve cover membrane of FIG. 7 with respect to its different mass, spring and damper locations.

As illustrated in the simplified model of FIG. 8A and the model of FIG. 8B, the drop section permits the membrane to have less mass and/or level of stiffness in the drop section region compared to the mass and/or level of stiffness of other areas or sections of the membrane, such as other areas in the central cap region 726. This effectively de-couples the different sections, therefore creating two spring-mass-damper systems, each having its own, different, natural (resonant) frequency. Thus, it reduces coupling between driving pressure and system response, creating a system that is far more difficult to excite at a resonance.

Thus, as illustrated in FIGS. 7, 8A and 8B, the first drop section provides a spring-mass-damper system characteristic 840-1 that is different from the spring-mass-damper system characteristic 840-R of the remainder of the cover membrane. Thin sections have less mass and less stiffness than thicker sections. Thinner section(s) respond faster than the heavy stiffer section(s). Therefore the build-up in pressure (e.g., positive end expiratory pressure PEEP) is reduced and so less kinetic energy is transferred in the mass "m". With the thin and thick sections being different, they resonate at different rates, reducing a likelihood of achieving system resonance, and result in a quieter cover membrane. In some cases, such as at 20 to 1 L/min of valve flow rate, a membrane comprising a drop section has been found to be quieter than a plain flat membrane (e.g., as shown in FIG. 2) with noise range between 35-55 decibels over the 1-12 cmH$_2$O, especially over 1-8 cmH$_2$O, which is a typical operating pressure range of an expiratory valve. There is also an additional benefit that the resulting noise is less tonal, and therefore subjectively less loud/intrusive to human ears even at the same decibel level.

The orientation of the membrane cover when installed can be significant, since the membrane cover may act unpredictably if the exhaust section of the valve overlaps partly with the thin section of the membrane. For this reason, the membrane cover may include orientation markers to assist with assembly during manufacturing. Thus, the markers may ensure or assist that the membrane cover is installed so that a drop section(s) are aligned away from an exhaust flow region where exhaust flow is intended to escape from the aperture at the valve seat. For example, a marker may be configured for use by a machine and/or an operator during assembly.

In some alternate versions of the present technology, rather than implementing a drop section(s), changes in operational noise characteristics of the membrane may be implemented by a simple constant ramp or tapering of the membrane thickness from one side to the next. However, such ramping can have disadvantages. First, simple membrane tapering can result in leaks. Having leaks is not desirable and embodiments herein can avoid such leaks. Second, the gradual change in thickness of tapering still permits vibration waves to propagate smoothly through the membrane. The discontinuity in thickness of a drop section, and in particular in relation to its ridge of deviation, produces a reflection location for the membrane wave so as to decouple the two masses (i.e., a drop section and another section adjacent to the drop section). Thus, the acoustic flow of air coupled to the membrane can be more affectively reduced with one or more drop sections.

Figure 9:
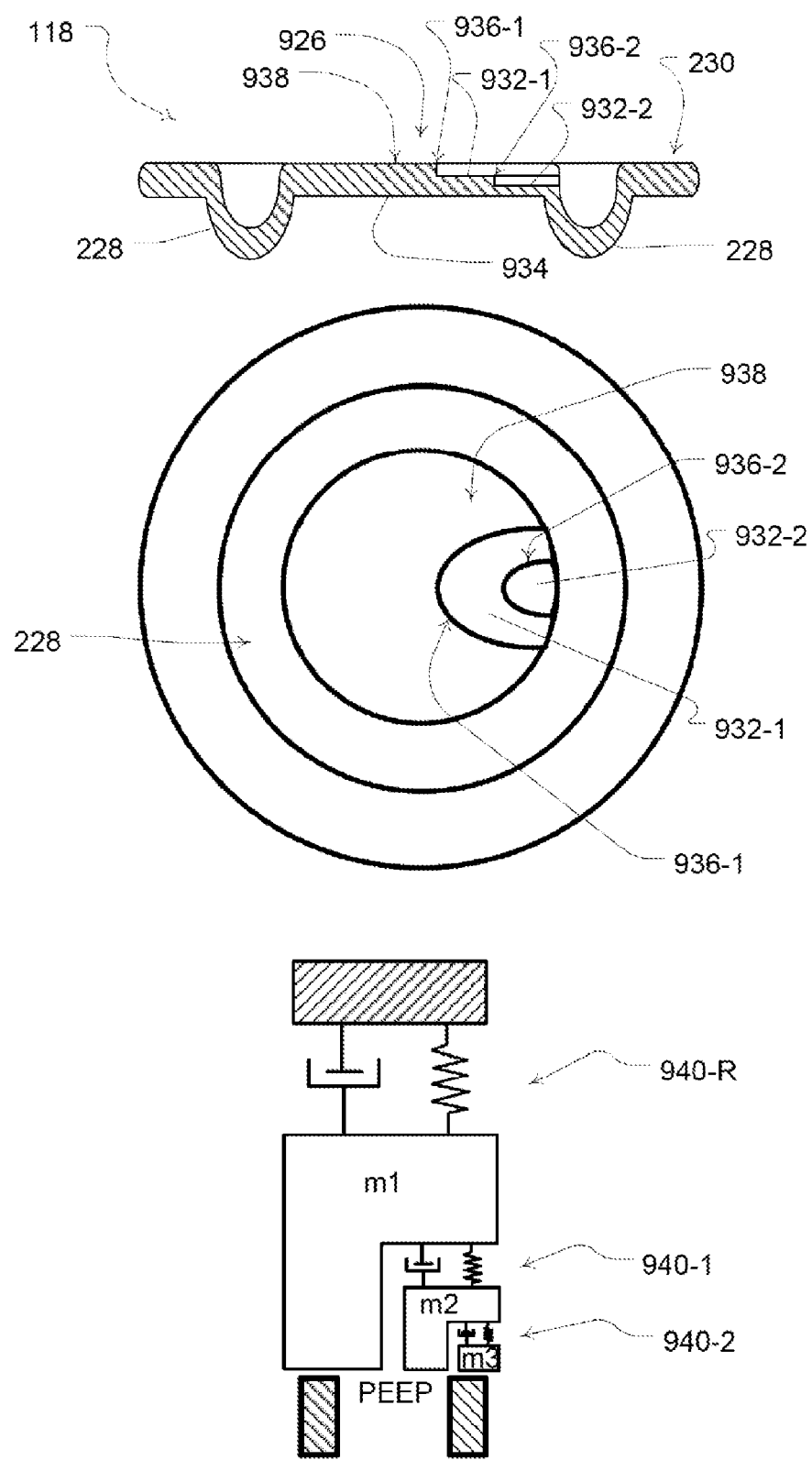
FIG. 9 is an illustration of a plan view and diameter cross sectional view of a modified valve membrane having multiple drop sections to change an operational characteristic of the membrane. The figure also illustrates a model of the operational characteristics with respect to its different mass, spring and damper locations.

In this regard, in some versions, two or more drop sections may be implemented in the membrane cover, such as in the central cap region. Moreover, in some cases, such drop sections may optionally be nested such that a drop section includes one or more drop sections (e.g., a nested drop section). Such a version may be considered in relation to model and membrane cover of FIG. 9. In this version, a first drop section is formed in the central cap region 926 of the cover membrane on its pressure chamber surface side 938, which is the surface side of the membrane cover that is opposite the valve seat surface side 934). The first drop section 932-1 includes a second drop section 932-2. In this case, each drop section includes a ridge 936-1, 936-2 of deviation about its relative section surface. In this version, the thickness of the second drop section is less than the thickness of the first drop section and the thickness of the first drop section is less than a thickness (e.g., a maximum thickness) of the cover membrane in the cap region. As illustrated in FIG. 9, the second drop section provides a spring-mass-damper system characteristic 940-2 that is different from the spring-mass-damper system characteristic 940-1 of first drop section, which in turn is different from the spring-mass-damper system characteristic 940-R of the remainder of the cover membrane.

Figure 10A:
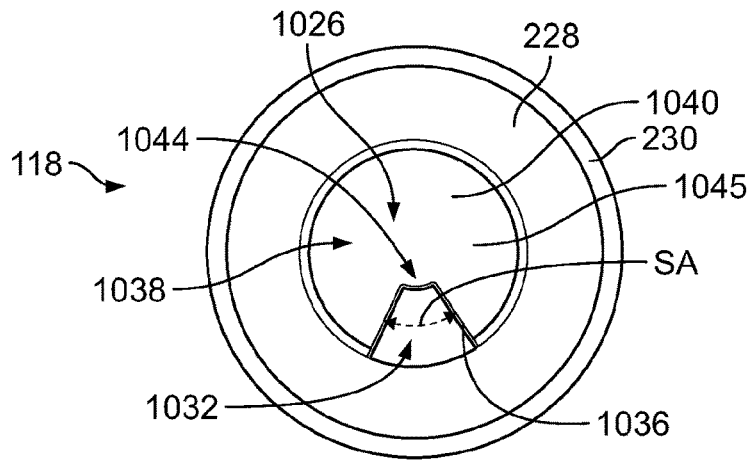
FIG. 10A is a plan view of a valve cover membrane having a unitary drop section formed as a sector with an acute angle.

FIGS. 10A to 10F illustrate various example flexible covers with one or more drop sections. In the examples, each drop section is formed as, or comprises, in a plan view, a sector of the cap region of the membrane cover. The sector may be an area of the surface of the membrane cover generally bounded by two radii associated with the sector edges, such as along the ridge of deviation previously described, and an arc of an outer edge of a circular cap region of the membrane cover. This outer edge may be an inside edge of the bellows region 228. Side ridges of the ridge 1036 of deviation (at the peripheral edge of deviation of the section) may form a sector angle SA (e.g., degrees) which may be any angle, and may be acute or obtuse. For example, as illustrated in FIG. 10A, a drop section 1032 forms a sector of approximately sixty degrees. Other sector angle sizes may be suitable (e.g., ten degrees, twenty degrees, twenty five degrees, one hundred eighty etc.). The remainder of the central cap region 1026 may form a raised section 1040 in the form of a sector. In FIG. 10A the sector is approximately three hundred degrees. The raised section may have a generally greater membrane thickness than the membrane thickness of the drop section. In this version, the drop section may begin outside of the center 1045 of the membrane. Optionally, as illustrated in FIGS. 10A to 10F, the ridge of the drop section at the center 1045 area of the cover membrane may be characterized as convex ridge 1044 along its ridge surface. However, alternatively, in some versions the ridge may be a concave ridge, or another profile, such as a straight line.

Figure 10B:
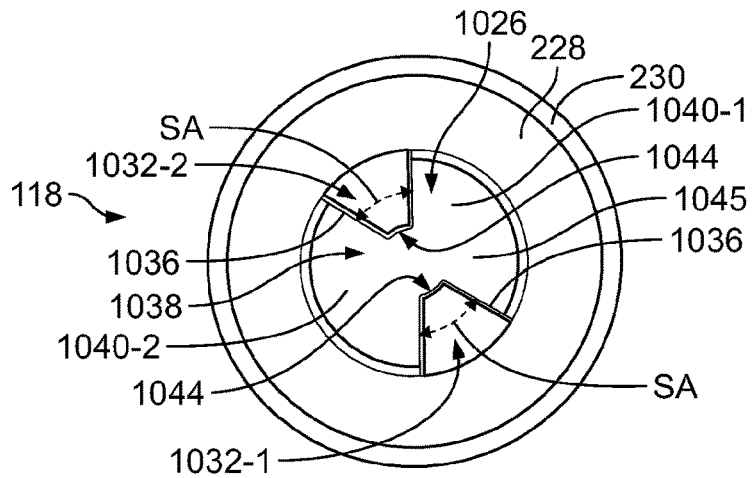
FIG. 10B is a plan view of a valve cover membrane having a plurality of drop sections formed as sectors on opposing sides of center of the membrane and having approximately equal sector surface area size.

The version of FIG. 10B is similar to that of FIG. 10A. However, two drop sections 1032-1, 1032-2 of the same area size (in plan view) are formed as sectors of approximately sixty degrees each. The drop sections may have equal dimensions. The thickness of the membrane (i.e., the cross sectional depth) of each of these drop section sectors may be the same or different. The sectors may be formed symmetrically opposite each other on the pressure chamber surface side 1038 of the membrane. In this version, raised sections 1040-1, 1040-2 are formed symmetrically on the remainder of the central cap region 1026 in the form of sectors of approximately one hundred twenty degrees each.

Figure 10C:
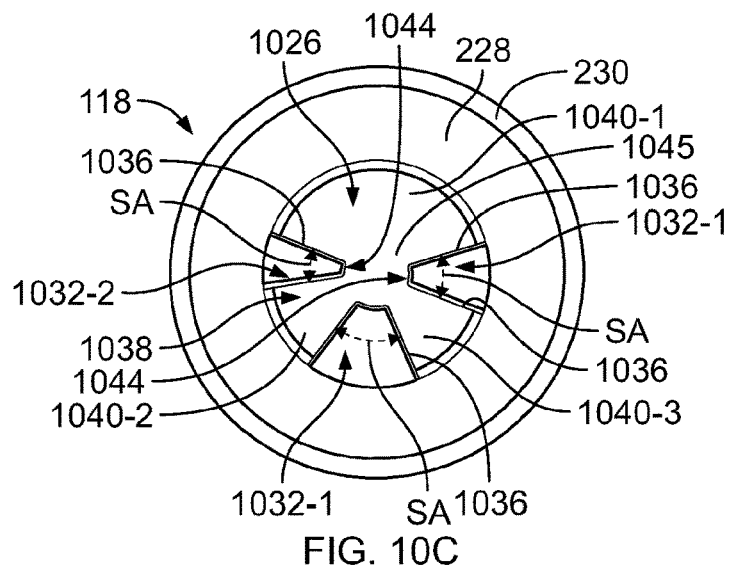
FIG. 10C is a plan view of a valve cover membrane having a plurality of drop sections formed as sectors with different sector surface area sizes.

The version of FIG. 10C is similar to that of FIG. 10B. However, the drop sections are formed of different sector area sizes. The thickness of the membrane of each of these sectors may be the same or different. As illustrated in the example of FIG. 10C, the drop sections 1032-1, 1032-2 and 1032-3 are formed by sectors of approximately thirty degrees, forty degrees and sixty degrees. The raised sections 1040-1, 1040-2 and 1040-3 may be formed as sectors, or raised sectors, of various sizes depending on location of the drop sections. In this version, since the drop sections are sectors located asymmetrically, the raised sections are raised sectors that may be similarly asymmetrically located. In this version, the raised sectors are approximately forty degrees, forty degrees and one hundred fifty degrees. Other raised sector sizes may be implemented.

Figure 10D:
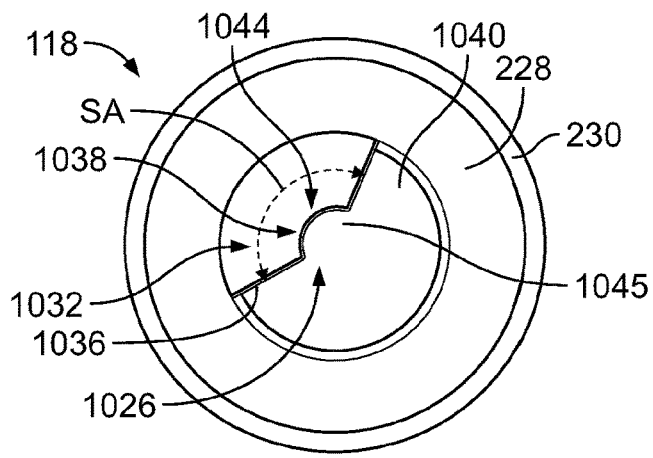
FIG. 10D is a plan view of a valve cover membrane having a unitary drop section formed as a sector with an obtuse angle.

The version of the flexible cover of FIG. 10D is similar to the prior versions. However, in this version a single drop section is formed in a sector of approximately one hundred forty degrees. The raised section is formed as a sector of approximately two hundred and twenty degrees. Other sector sizes may be implemented.

Figure 10E:
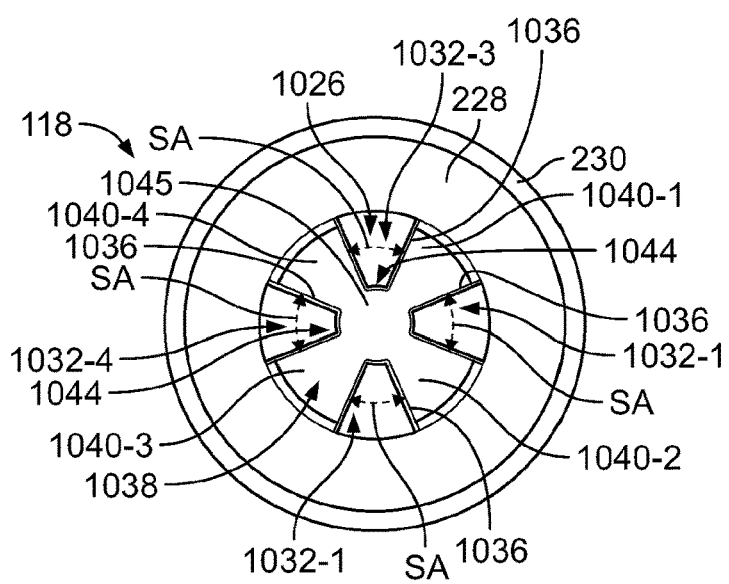
FIG. 10E is a plan view of a valve cover membrane having a plurality of drop sections formed as sectors on opposing sides of center of the membrane and having approximately equal sector surface area size.

The version of FIG. 10E is similar to the prior versions. However, in this version the cap region sections may be formed of sectors of approximately the same size. In this version, four drop sections 1032-1, 1032-2, 1032-3 and 1032-4 and four raised sections 1040-1, 1040-2, 1040-3 and 1040-4 are formed in sectors, each having a sector angle size of approximately forty five degrees. The thickness of each drop section may be the same or different. Similarly, the thickness of each raised section may be same or different.

Figure 10F:
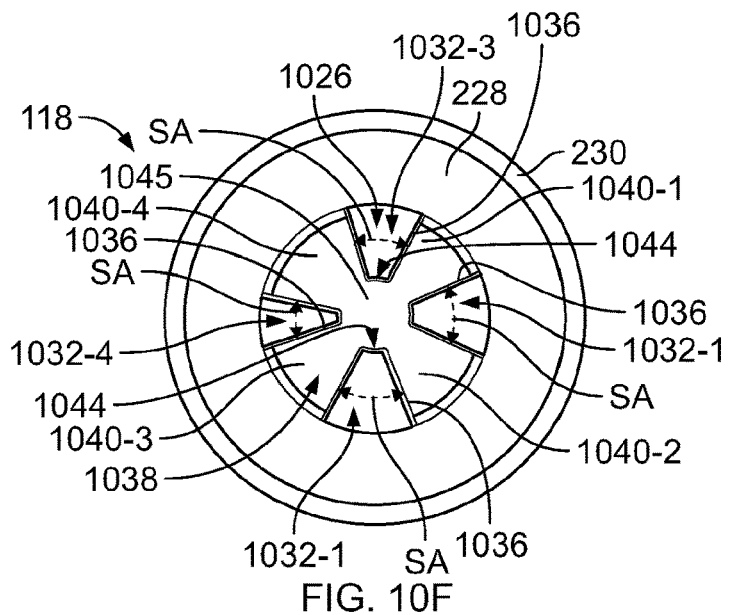
FIG. 10F is a plan view of a valve cover membrane having a plurality of drop sections formed as sectors on opposing sides of center of the membrane and having different sector surface area sizes.

The version of FIG. 10F is similar to the version of FIG. 10D. However, in this version four drop sections 1032-1, 1032-2, 1032-3 and 1032-4 are included, each of different sector area sizes. In this version, the drop sections are formed of sectors angle sizes of approximately thirty degrees, forty degrees, fifty degrees and sixty degrees. The raised sections 1040-1, 1040-2, 1040-3 and 1040-4 may be formed as sectors of various sizes. For example in this version the raised sectors are approximately the same sector angle sizes as the drop section sectors. However, in some versions they may be different. As illustrated, the raised section sectors are approximately thirty degrees, forty degrees, fifty degrees and sixty degrees.

Figure 11A:
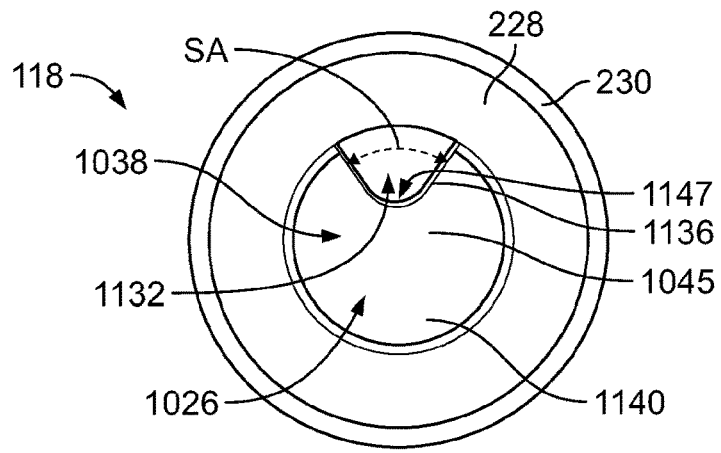
FIGS. 11A, 11B and 11C illustrate further example valve cover membranes having various drop sections.
Figure 11B:
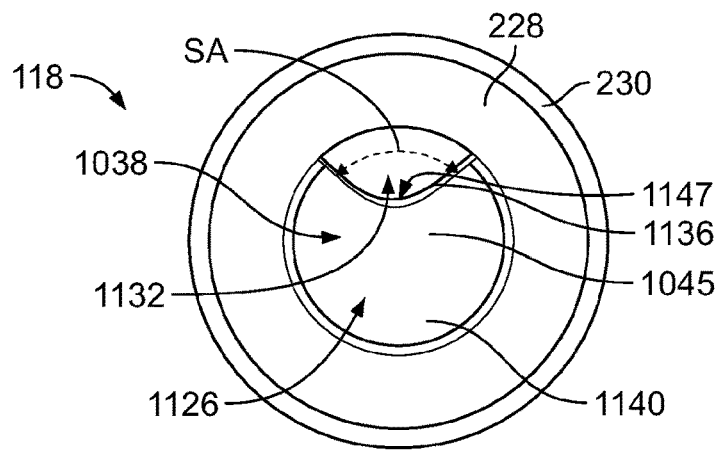
Figure 11C:
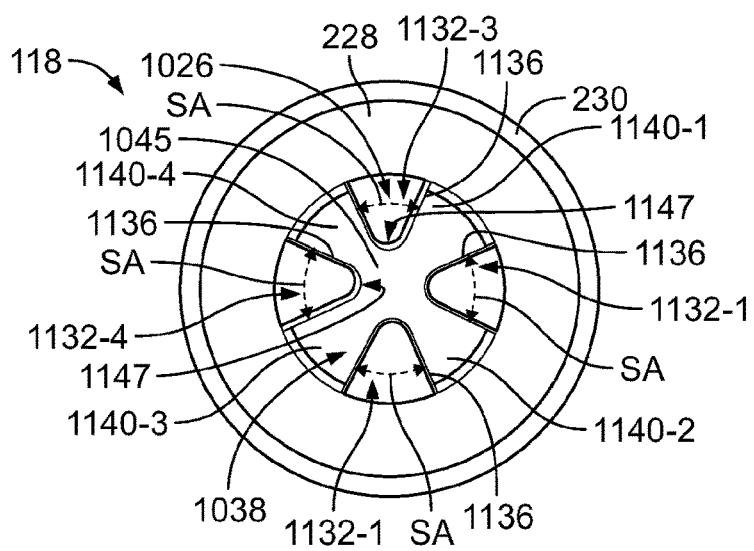

FIGS. 11A to 11C illustrate various example flexible cover membranes with one or more drop sections. These cover membranes are similar to the versions previously described, such as in relation to the description of FIGS. 10A-10F, unless otherwise specified below. As illustrated in FIG. 11A, a single drop section 1132 is formed as a sector having, for example, an acute sector angle SA. In the example, the sector is approximately sixty degrees. The raised section 1140 is formed as a sector of approximately three hundred degrees. The ridge 1136 of deviation along the periphery of the drop section forms the concave ridge 1147 in the center 1045 area of the cover membrane.

In the version of FIG. 11B, the drop section is formed by a ridge 1136 that is generally curved across the central cap region 1126 of the cover membrane. At its center the curved ridge may be characterized as a concave ridge 1147 of the drop section. The area of the drop section 1132 of FIG. 11B may be approximately to the area of a sector of one hundred forty degrees. The area of the raised section 1140 of FIG. 11B may be approximately to the area of a sector of two hundred twenty degrees.

The flexible cover membrane version of FIG. 11C is similar to the version of FIG. 11A. However, in this version, the membrane includes four drop sections 1132-1, 1132-2, 1132-3 and 1132-4 comprising sectors of approximately forty five degrees each. Like FIG. 11A, at the cover center CA, the ridge of each drop section may be characterized as a concave ridge 1147 of the drop section. The area of the raised sections 1140-1, 1140-2, 1140-3 and 1140-4 of FIG. 11C may each have a size of approximately the area of a sector of forty five degrees.

It is noted that, a flexible cover membrane may comprise a drop section in different shapes than those of sectors of various angles as shown above. It will be understood that drop sections of other shapes may be configured to comprise less mass and less stiffness than adjacent section(s), to de-couple the drop section from the adjacent section.

Figure 12:
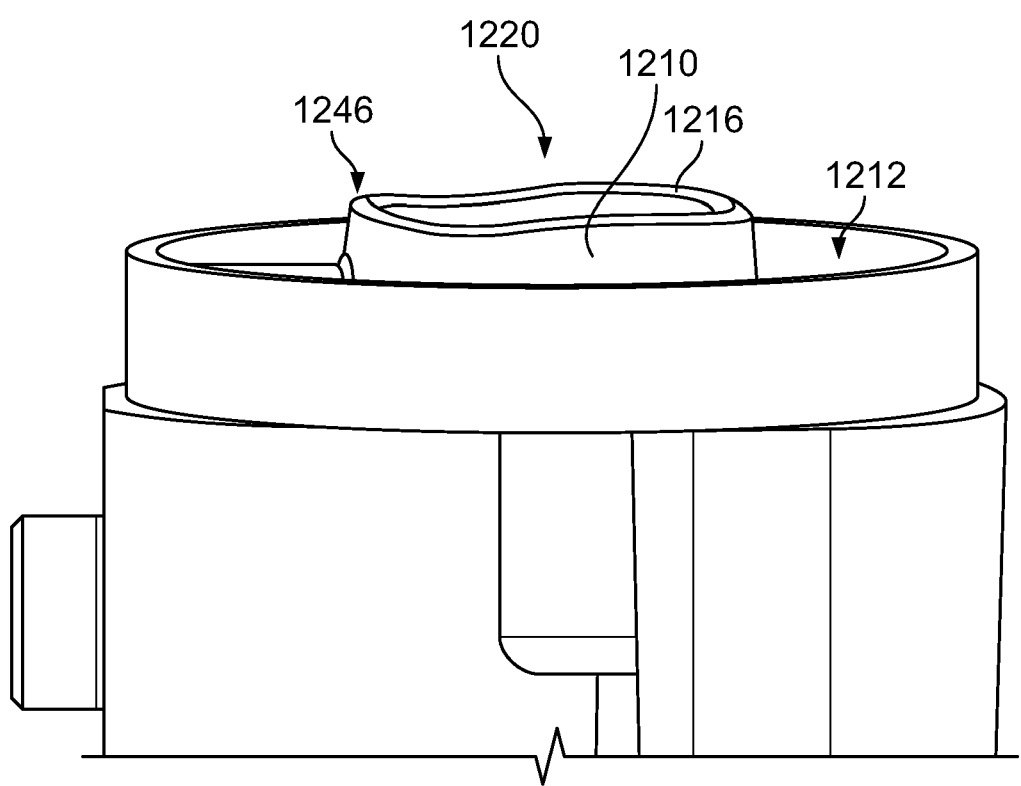
FIG. 12 is a isometric view of a portion of a valve illustrating a wavy valve seat surface suitable for some versions of the present technology.

While the aforementioned modified valve membrane embodiments may be implemented to reduce noise outputs of the valve in use, in some versions of the present technology additional and/or alternative aspects may be implemented to reduce noise outputs of the valve in use, such as noise generated by a membrane of the valve. For example, as shown in the partial valve illustration of FIG. 12, a peripheral surface of the valve seat 1216 that defines the aperture 1220 between the inlet 1210 and the outlet 1212 of the valve may be profiled for noise reduction. For example, any of the aforementioned cover membranes may be implemented in a valve assembly having with a variable valve seat. In these versions, the cover contact surface or rim 1246 of the valve seat 1216 may comprise a variation in height along a circumferential direction. For example, in relation to an imaginary plane defined by the first side surface of the flexible gas passage cover. For example, as illustrated in FIG. 12, the rim 1246 of the valve seat may have a wavy form (e.g., a wavy or non-planar rim/surface), comprising for example a regular (e.g. a sine wave) or an irregular (e.g.

shown in FIG. 12) variation in height. The wavy surface may vary in height about the circumference of the valve aperture 1220. This can result in a quieter membrane performance because some of the air pressure on the patient side or valve seat surface side of the membrane is released before all the masses have moved, thus avoiding resonance. The depth of the waviness of the rim may depend on the flexibility of the cover membrane as the two should be configured to ensure the valve can be fully closed (i.e., the membrane cover should fully seal with the contact surface of the complete periphery of the rim of the valve seat.)

In some versions of the present technology, still further or alternative modifications may be implemented to reduce noise characteristics of the valve. For example, any of the aforementioned membrane or valve components may be implemented in a valve assembly that includes a coated membrane cover. For example, a side surface of the flexible cover membrane, such as the valve seat surface side, may include a coating to reduce a coefficient of friction of a membrane material. For example, the membrane may include a coating to reduce the coefficient of the friction of the membrane to allow the membrane to respond faster and release the build-up of pressure. For example, a coating of talcum powder or a silicone dispersion may be implemented on the flexible cover membrane. A suitable example coating may be any of Slick SIL™ LSR from Surface Solutions group Inc. or MED-6670 or MED-6671 both from NuSil Silicone Technology.

Example Respiratory Treatment Apparatus

Figure 13:
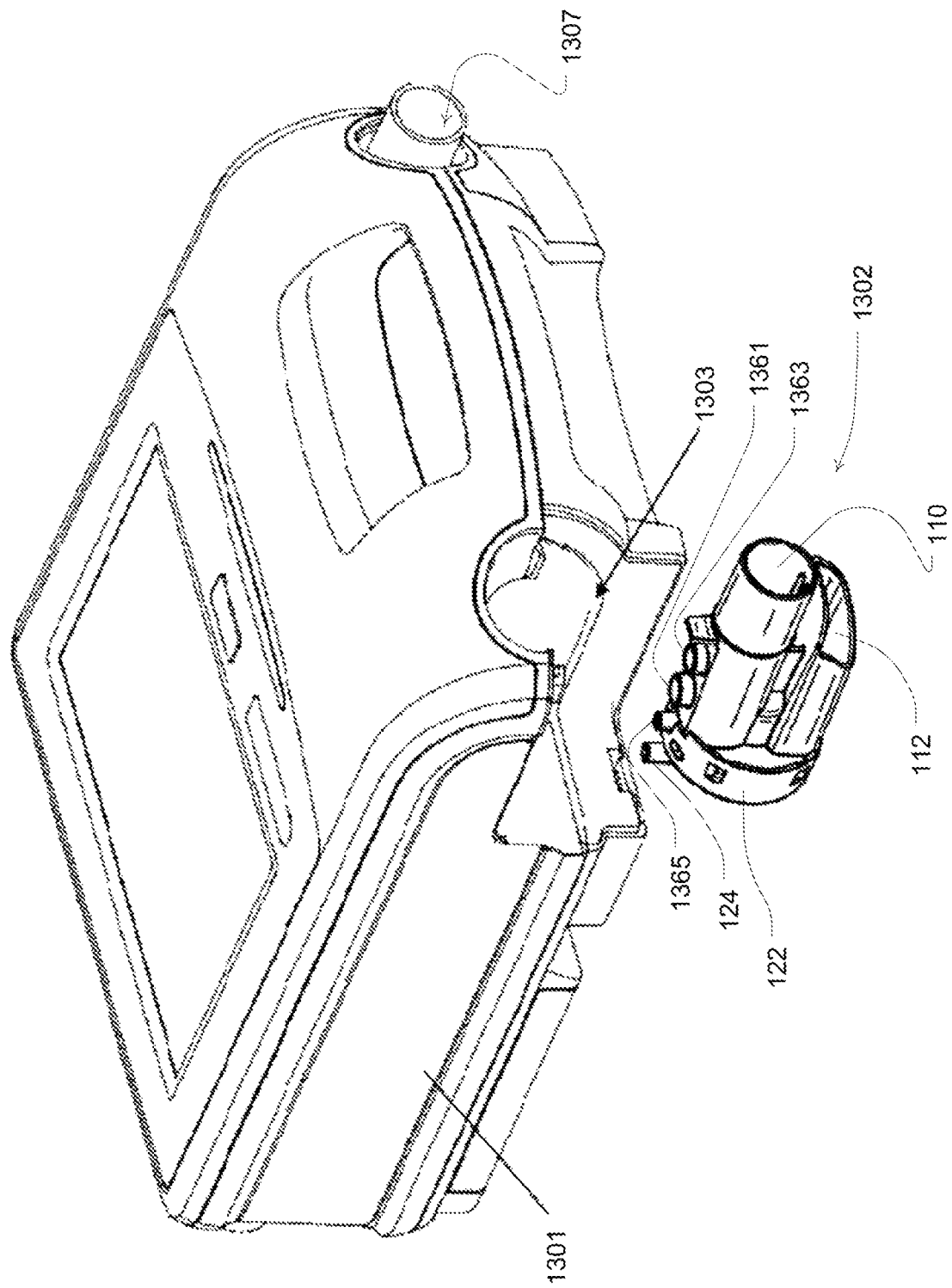
FIG. 13 shows an example respiratory pressure therapy apparatus (RPT), such as a ventilator, having a removable breathable gas valve device configured as an expiratory valve.
Figure 14:
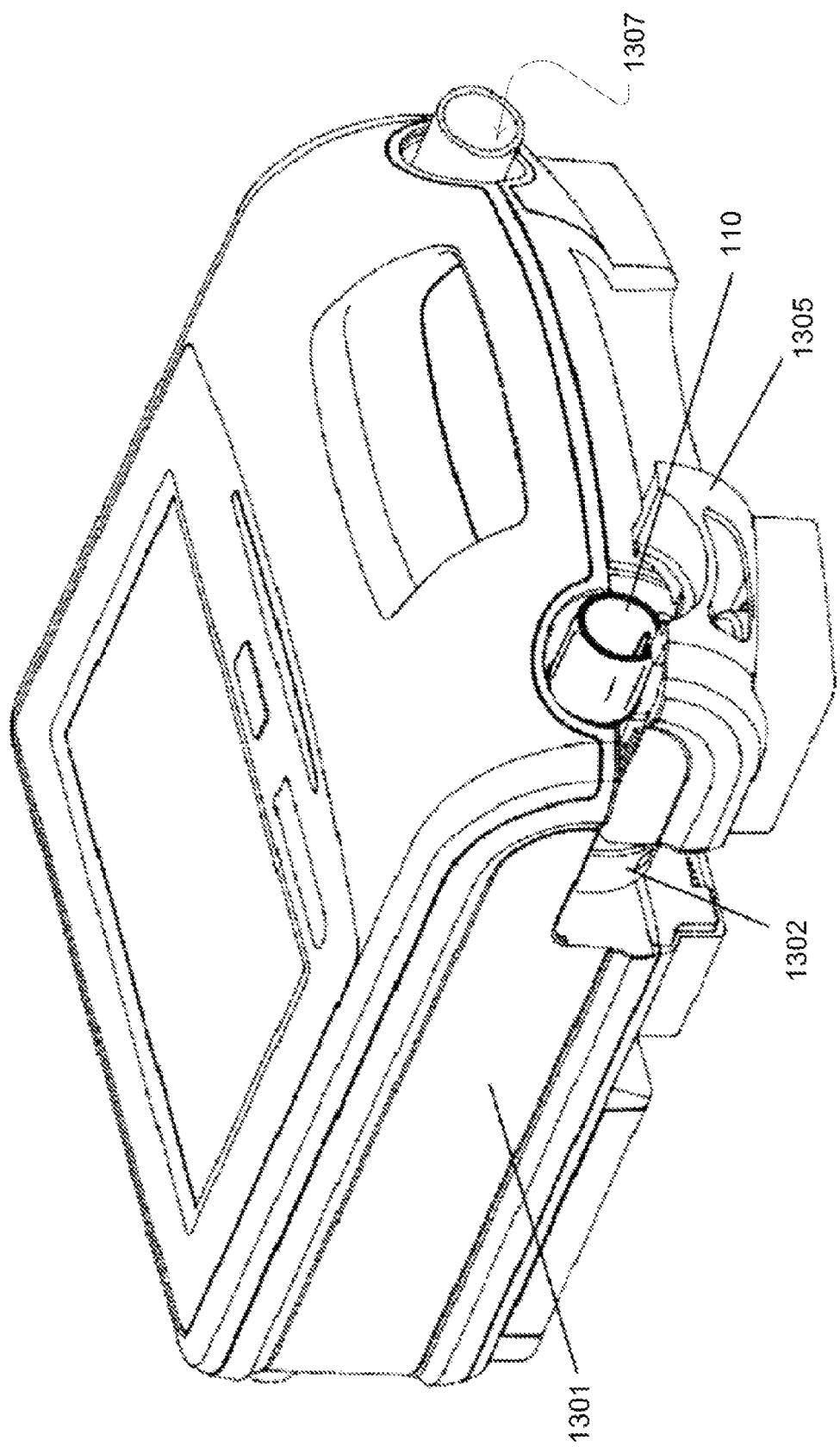
Figure 15:
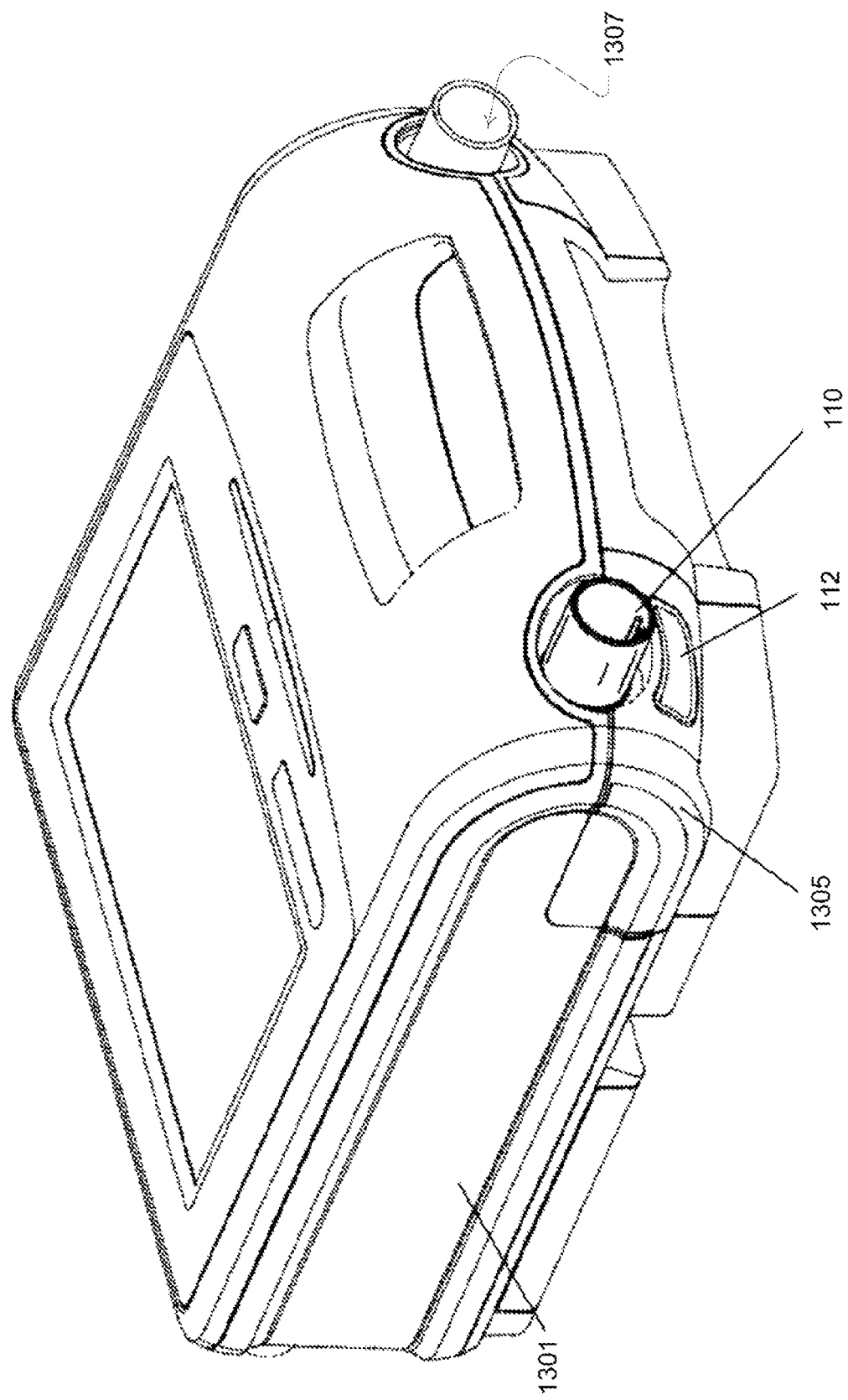
FIG. 15 shows the removable gas valve device of FIG. 13 fully installed in the RPT.

As previously discussed, the breathable gas control valve device 102 may be implemented in a respiratory treatment apparatus 1301, such as the ventilator or continuous positive airway pressure device illustrated in FIGS. 13, 14 and 15. Such an apparatus includes a controller (not shown), with one or more microcontrollers or processors, such as so that the respiratory treatment apparatus may be configured with one more treatment regimes for setting the pressure delivered by the pressure generator(s) or blower(s) in conjunction with signals from optional pressure sensors(s) and/or flow sensor(s). Thus, the controller may adjust the speed of the blower(s) during patient treatment to treat detected conditions (e.g., flow limitation, inadequate ventilation, apnea, etc.) and/or synchronize pressure changes during detected patient respiration to simulate or support respiration. Thus, the controller may be configured to selectively set the pressure of the pressure chamber by control of one or more flow control valves or a positive end expiratory pressure blower to control end expiratory pressure with the breathable gas control valve device 102 when implemented as an expiratory valve, such as the expiratory valve 1302 illustrated in FIG. 13. The valve 1302 may be installed within a valve compartment 1303 and secured with compartment lid 1305.

Thus, the controller will typically include one or more processors configured to implement particular control methodologies. To this end, the controller may include integrated chips, a memory and/or other control instruction, data or information storage medium. For example, programmed instructions encompassing such a control methodology may be coded on integrated chips in the memory of the device. Such instructions may also or alternatively be loaded as software or firmware using an appropriate data storage medium. The controller will also typically include a bus or electronic interface for setting the flow control valves as well as the other components of the apparatus (e.g., blower motor).

For example, one or more blowers (not shown), such as a servo-controller blower, will include a motor, volute and impeller. With the impeller, the blower can, for example, produce a pressure in the pressure chamber 122 of the expiratory valve via the pressure conduit 124. The respiratory treatment apparatus may also have a blower to produce a respiratory pressure treatment to a gas outlet 1307 which will typically be configured for coupling with a patient circuit for connection to a patient interface for respiratory treatment. A patient circuit may also be referred to as a delivery or supply conduit, and suitable examples of a patient interface may include a mask or tracheotomy tube (not shown). An expiratory conduit from the patient circuit (not shown) may then provide exhaled air from the patient interface to the inlet 110 of the expiratory valve 1302. Differential pressure sensing ports 1361 and 1363 permit sensing of expiratory flow through the expiratory valve with a flow sensor or differential pressure sensor (not shown). An expiratory pressure sensing port 1365 in pneumatic communication with pressure sensor (not shown)) permits sensing of expiratory pressure in the expiratory valve. As illustrated in FIGS. 14 and 15, the expiratory valve may be inserted as a removable module, within the respiratory treatment apparatus in a compartment for the module.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A valve device for a gas passage of a respiratory treatment apparatus that is configured to provide a flow of breathable gas to a patient, the valve device comprising:
    a valve seat defining an aperture of the gas passage for the flow of breathable gas; and
    a flexible gas passage cover, the cover comprising a first side surface to operatively block and open the aperture of the gas passage at the valve seat to respectively prevent and permit gas flow through the aperture of the gas passage,
    the flexible gas passage cover further comprising a second side surface opposite the first side surface,
    wherein the cover comprises at least one drop section including a reduction in a thickness between the first side surface and the second side surface, the at least one drop section being formed in at least a flexible portion of a central cap region of the flexible gas passage cover, wherein the central cap region is positioned relative to the valve seat so as to block and open the aperture of the gas passage in use.

2. The valve device of claim 1 wherein the cover comprises a plurality of drop sections.

3. The valve device of claim 2 wherein each drop section of the plurality of drop sections comprises a sector.

4. The valve device of claim 1 wherein the cover comprises a plurality of first sectors and a plurality of second sectors, the first sectors being raised in relation to the plurality of second sectors.

5. The valve device of claim 4 wherein the plurality of first sectors comprises four sectors.

6. The valve device of claim 4 wherein the plurality of second sectors comprises four sectors.

7. The valve device of claim 2 wherein the drop sections of the plurality of drop sections have equal dimensions.

8. The valve device of claim 1 wherein a drop section includes a nested drop section.

9. The valve device of claim 1 further comprising the gas passage and the valve seat within a removable module.

10. The valve device of claim 1 wherein the gas passage is configured as an expiratory gas passage.

11. The valve device of claim 1 wherein the gas passage is configured as an inspiratory gas passage.

12. The valve device of claim 9 further comprising a pressure chamber adjacent to the second side surface of the cover to apply a confined operational gas pressure to the second side surface of the cover.

13. The valve device of claim 1 wherein the flexible gas passage cover is configured as a circular disk.

14. The valve device of claim 13 wherein the circular disk includes a peripheral ring and wherein the valve seat comprises a circular rim.

15. The valve device of claim 1 wherein the first side surface of the cover comprises a coating to reduce a coefficient of friction of a membrane material of the first side surface of the flexible gas passage cover.

16. The valve device of claim 1 wherein the valve seat comprises a cover contact rim, the cover contact rim comprising a variation in height in relation to an imaginary plane formed by the first side surface of the flexible gas passage cover.

17. A positive airway pressure apparatus comprising:
    a flow generator adapted to provide a supply of pressurized breathable gas to a patient interface; and
    a controller to control a level of pressure generated by the flow generator,
    the positive airway pressure apparatus further comprising a valve device of claim 1.

* * * * *